United States Patent [19]

Jernberg

[11] Patent Number: 5,290,271
[45] Date of Patent: Mar. 1, 1994

[54] SURGICAL IMPLANT AND METHOD FOR CONTROLLED RELEASE OF CHEMOTHERAPEUTIC AGENTS

[76] Inventor: Gary R. Jernberg, 99 Navaho Ave. Suite 102, Mankato, Minn. 56001

[21] Appl. No.: 99,265

[22] Filed: Jul. 29, 1993

Related U.S. Application Data

[63] Continuation of Ser. No. 899,096, Jun. 15, 1992, abandoned, which is a continuation of Ser. No. 599,699, Oct. 18, 1990, abandoned, which is a continuation-in-part of Ser. No. 523,067, May 14, 1990, abandoned.

[51] Int. Cl.$^5$ .............................................. A61K 9/22
[52] U.S. Cl. ................................. 604/891.1; 623/13; 623/11; 424/473
[58] Field of Search ........................... 623/11, 13, 16; 604/890.1, 891.1; 424/469–473

[56] References Cited

U.S. PATENT DOCUMENTS

| | | |
|---|---|---|
| 4,226,848 | 10/1980 | Nagai et al. . |
| 4,249,531 | 2/1981 | Heller et al. . |
| 4,292,299 | 9/1981 | Suzuki et al. . |
| 4,321,711 | 3/1982 | Mano . |
| 4,524,065 | 6/1985 | Pinnell .................................. 424/94 |
| 4,536,387 | 8/1985 | Sakamoto et al. .................... 514/781 |
| 4,568,536 | 2/1986 | Kronenthal et al. ................. 514/965 |
| 4,645,668 | 2/1987 | Pinnell .................................. 424/94 |
| 4,650,665 | 3/1987 | Kronenthal et al. ................. 424/435 |
| 4,657,548 | 4/1987 | Nichols ................................ 623/10 |
| 4,685,883 | 8/1987 | Jernberg . |
| 4,703,108 | 10/1987 | Silver et al. .................... 128/DIG. 8 |
| 4,713,243 | 12/1987 | Schiraldi et al. .................... 424/151 |
| 4,745,161 | 5/1988 | Saudek et al. . |
| 4,752,294 | 6/1988 | Lundgren . |
| 4,764,377 | 8/1988 | Goodson ............................ 424/443 |
| 4,776,890 | 10/1988 | Chu .................................... 433/201.1 |
| 4,780,320 | 10/1988 | Baker .................................. 424/493 |
| 4,789,662 | 12/1988 | Thomas-Leurquin et al. ...... 514/801 |
| 4,789,663 | 12/1988 | Wallace et al. ..................... 514/21 |
| 4,795,467 | 1/1989 | Piez et al. ........................... 623/16 |
| 4,804,744 | 2/1989 | Sen . |

(List continued on next page.)

FOREIGN PATENT DOCUMENTS

| | | |
|---|---|---|
| 0126453 | 4/1987 | European Pat. Off. . |
| 0224987 | 6/1987 | European Pat. Off. . |
| 0293090 | 11/1988 | European Pat. Off. . |
| 0406665 | 1/1991 | European Pat. Off. . |
| 2033232 | 5/1980 | United Kingdom . |

(List continued on next page.)

OTHER PUBLICATIONS

Heparan Sulfate and Fibronectin Improve the Capacity of Collagen Barriers to Prevent Apical Migration of the Junctional Epithelium Authors: S. Pitaru, M. Noff, A. Grosskofp, O. Moses, H. Tal, and N. Savion J. Periondontal, Oct., 1991, 62:598, 601.
Aukhil et al., *J. Dent. Res.*, 66 (Spec. Issue Mar.): 281, Abstr.
Busschop et al., *J. Clin. Periodontal.*, 10:399–411 (1983).
Caffesse et al., *J. Dent Res.*, 66 (Spec. Issue Mar.): 281.
Dahlin et al., *Plastic and Reconstructive Surg.*, 81(5): 672–676 (1988).
El Deeb et al., *J. Dent. Res.*, 65 (Spec. Issue B): 822, Abstr. 864 (1986).
Fleisher et al., *J. Dent. Res.*, 66 (Spec. Issue Mar.): 281, Abstr. 1393 (1987).
Gottlow et al., *J. Dent. Res.*, 66 (Spec. Issue Mar.): 281, Abstr. 1394 (1987).
Kenney et al., *J. Dent. Res.*, 65 (Spec. Issue B): 822, Abstr. 867 (1986).
Magnusson et al., *J. Dent. Res.*, 65 (Spec. Issue B): 822, Abstr. 866 (1986).

(List continued on next page.)

Primary Examiner—C. Fred Rosenbaum
Assistant Examiner—Ronald K. Stright, Jr.
Attorney, Agent, or Firm—Merchant, Gould, Smith, Edell, Welter & Schmidt

[57] ABSTRACT

An implant and method is disclosed using microparticles to provide a controlled, sustained release, and improved cellular uptake, of chemotherapeutic agents.

6 Claims, 3 Drawing Sheets

U.S. PATENT DOCUMENTS

| | | | |
|---|---|---|---|
| 4,816,339 | 3/1989 | Tu et al. | 428/421 |
| 4,828,563 | 5/1989 | Muller-Lierheim | 623/16 |
| 4,837,285 | 6/1989 | Berg et al. | 530/356 |
| 4,839,175 | 6/1989 | Guo et al. | 128/DIG. 8 |
| 4,841,962 | 6/1989 | Berg et al. | 128/DIG. 8 |
| 4,851,521 | 7/1989 | della Valle et al. | |
| 4,886,787 | 12/1989 | de Belder et al. | 514/57 |
| 4,892,516 | 1/1990 | Harle | |
| 4,946,377 | 8/1990 | Kovach | 623/13 |
| 5,032,445 | 7/1991 | Scantlebury et al. | |
| 5,077,049 | 12/1991 | Dunn et al. | |
| 5,092,841 | 3/1992 | Spears | 606/194 |
| 5,100,429 | 3/1992 | Sinofsky et al. | 606/193 |

FOREIGN PATENT DOCUMENTS

| | | |
|---|---|---|
| 2146525. | 4/1985 | United Kingdom . |
| 2103927 | 3/1987 | United Kingdom . |
| 87/06129 | 10/1987 | World Int. Prop. O. . |
| 8706129 | 10/1987 | World Int. Prop. O. . |

OTHER PUBLICATIONS

Maniar et al., "Polyanhydrides: V. Branched Polyanhydrides," *Biomaterials*, vol. 11, No. 9, Nov. 1990; pp. 690–694.

Niederman et al., *J. Dent. Res.*, 66 (Spec. Issue Mar.): 281, Abstr. 1392 (1987).

Othman et al., "The Effect of Chlorohexidine (CH)–Containing Coe-pak on Wound Healing After Gingivectomy," *J. Dent. Res.*, 65 (Spec. Issue B): 822, Abstr. 866 (1986).

Pitaru et al., *J. Dent Res.*, 65 (Spec. Issue B): 822, Abstr. 870 (1986).

Pontoriero et al., *J. Dent. Res.*, 67 (Spec. Issue Mar.): 272, Abstr. 1277 (1988).

Rabaud, "Elastin-Based Product and Its Biological Application Particularly as Biomaterial and an Artificial Support," *Chemical Abstracts*, vol. 105, 1986 (Columbus, Ohio); pp. 364, Col. 1, Abstr. No. 232443m.

Terranova et al., "Reconstituted Basement Membrane Inhibits The movement of Gingival Epithelial Cells to Dentin," *J. Dent. Res.*, 66 (Spec. Issue Mar.): 280 Abstr. 1390 (1987).

West et al., *J. Dent. Res.*, 67 (Spec. Issue Mar.) 273, Abstr. 1281 (1988).

Blumenthal et al., *J. Perodontal*, vol. 59, No. 12, 1988; pp. 830–836.

Aukhil et al., *J. Periodontal*, vol. 57, No. 12, 1986; pp. 727–734.

Levy et al., *J. Periodontal*, vol. 52, 1981; pp. 303–306.

Yaffe et al., *J. Periodontal*, vol. 55, No. 11, 1984; pp. 623–628.

Blumenthal et al., *J. Periodontal*, vol. 57, No. 2, 1986, pp. 84–90.

M. Minabe et al., 60, *J. Periodontol*, 113–117 (Feb. 1989).

E. Young and B. Sugarman, 68, *Surgical Clinics of N. America*, 167–181 (Feb. 1988).

N. Horbach et al., 71, *Obstetrics & Gynecology*, 648–652 (Apr. 1988).

N. Schoenfeld et al., 8, *Journal of Vascular Surgery*, 49–54 (Jul. 1988).

M. Reigel et al., 54, *The American Surgeon*, 134–136 (Mar. 1988).

L. Dacey et al., 8, *Journal of Vascular Surgery*, 21–27 (Jul. 1988).

S. Ahlfeld et al., 15, *The American Journal of Sports Medicine*, 326–330 (1987).

S. Hughes, 16, *Orthopaedic Review*, 233/59–235/61 (Apr. 1987).

B. van der Lei et al., 76, *Br. J. Surg.*, 803–805 (1989).

J. H. Roth et al., 16, *The American Journal of Sports Medicine*, 301–305 (1988).

T. Smith et al., 171, *Radiology*, 507–508 (1989).

A. Nordestgaard et al., *Current Surgery*, 490–493 (Nov.–Dec. 1987).

A. Amis et al., 70, *The Journal of Bone and Joint Surgery*, 628–634 (Aug. 1988).

P. Schreuders et al., 22, *Journal of Biomedical Materials Research*, 121–135 (1988).

N. Sevastjanova et al., 8, *Biomaterials*, 242–247 (Jul. 1987).

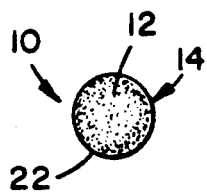 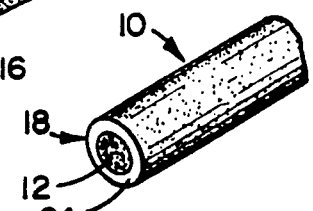 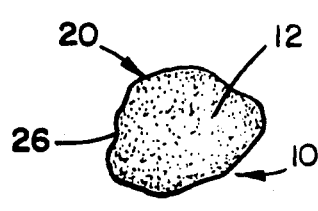
FIG. 1A  FIG. 1B  FIG. 1C  FIG. 1D
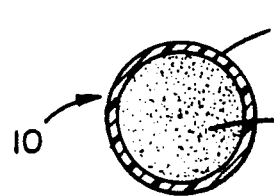 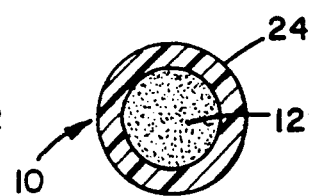 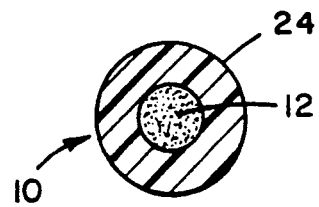
FIG. 2A  FIG. 2B  FIG. 2C
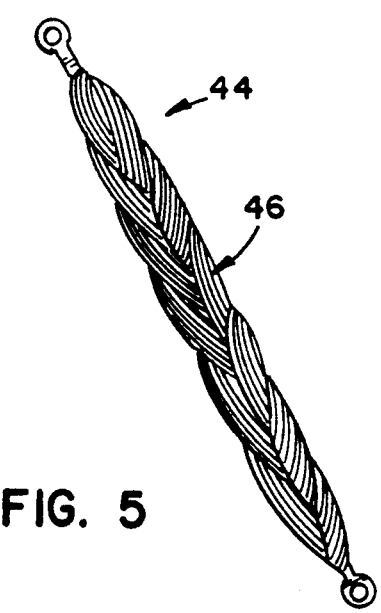
FIG. 5
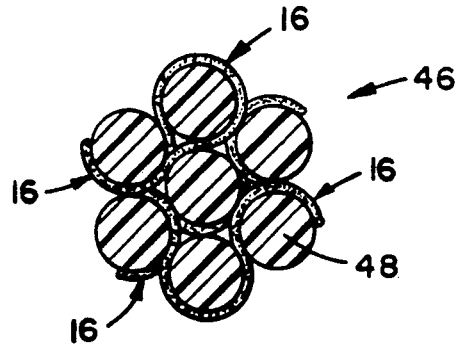
FIG. 6A
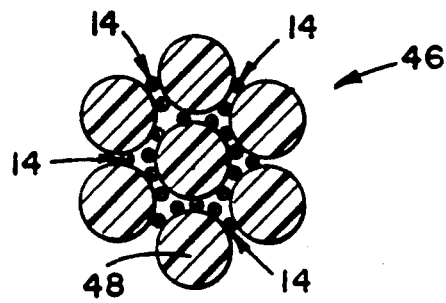
FIG. 6B FIG. 3
(PRIOR ART)
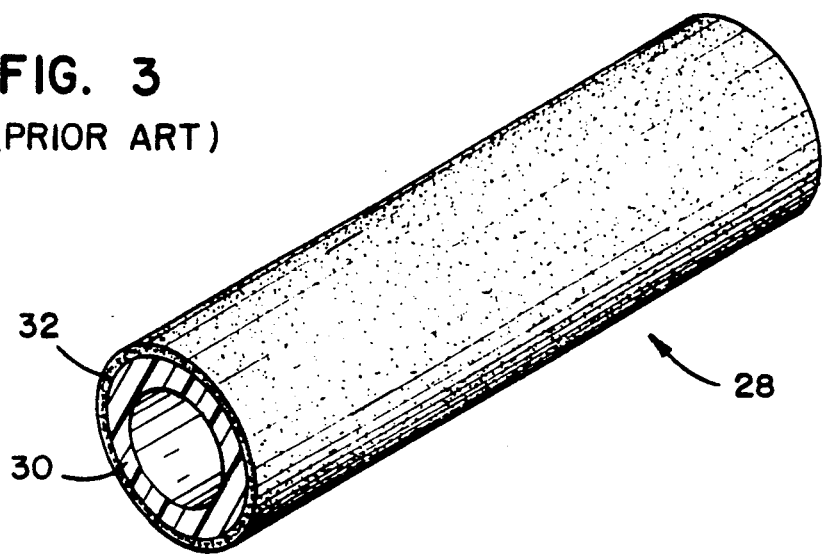
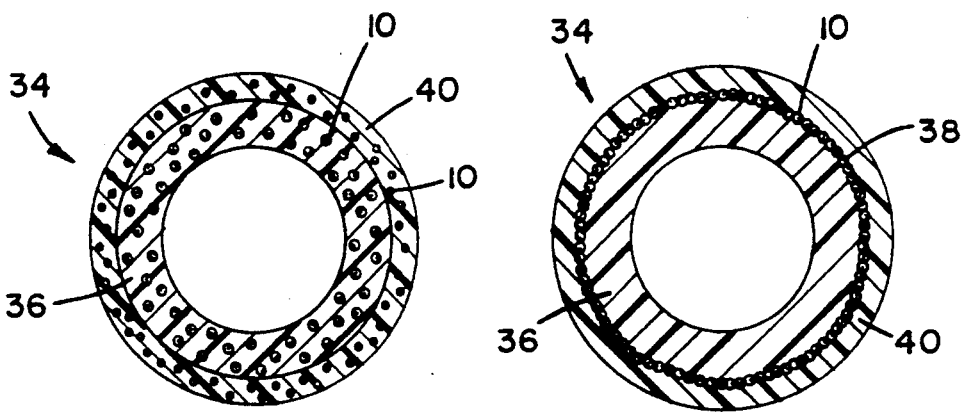
FIG. 4A  FIG. 4B
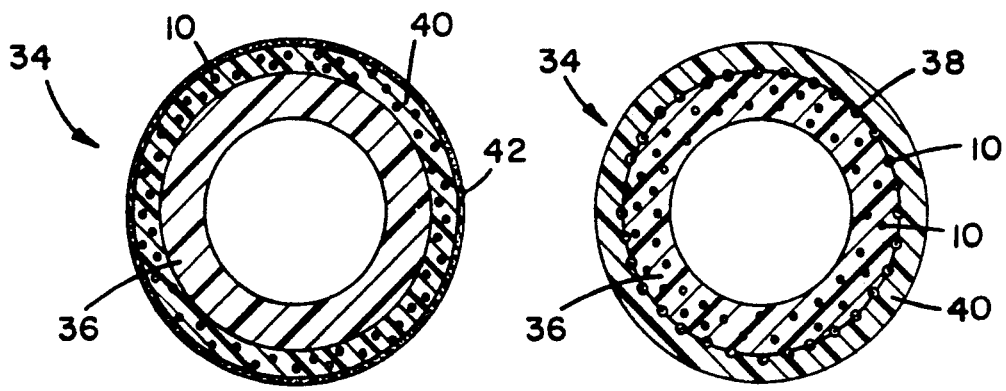
FIG. 4C  FIG. 4D

SURGICAL IMPLANT AND METHOD FOR CONTROLLED RELEASE OF CHEMOTHERAPEUTIC AGENTS

This is a continuation of application Ser. No. 07/899,096, filed Jun. 15, 1992, now abandoned, which is a continuation of application Ser. No. 07/599,699, filed Oct. 18, 1990, now abandoned, which is a continuation-in-part of application Ser. No. 07/523,067, filed May 14, 1990, now abandoned.

TECHNICAL FIELD OF THE INVENTION

The present invention relates to a surgical implant and method which provides for controlled release and improved cellular uptake of chemotherapeutic agents over a predetermined period of time.

BACKGROUND OF THE INVENTION

Biologically compatible materials capable of being formed into implants are increasing in use in surgery and medicine. Examples include vascular grafts, ligament prostheses and reconstructive patches.

Utilization of surgical implants presents several problems to the practitioner. For example, the potential of infections exists with surgically placed implants, including grafts, prostheses, etc. See e.g., E. J. Young and B. Sugarman, *Infections in Prosthetic Devices*, 68 Surg. Clin. N. Am., 167 (1988); *The International Journal of Periodontics and Restorative Dentistry*, April (1988); B. Van der Lei, et al., *Expanded Polytetrafluoroethylene Patch for the Repair of Large Abdominal Wall Defects*, 76 Br. J. Surg., 803 (1989); N. S. Horbach, et al., *A Suburethral Sling Procedure with Polytetrafluoroethylene for the Treatment of Genuine Stress Incontinence in Patients with low Urethral Closure Pressure*, 71 Obstete. Gynecol., 648 (1988).

Adverse clotting problems can also occur with vascular grafts. N. A. Schoenfeld, et al., *A New Primate Model for the Study of Intravenous Thrombotic Potential and its Modification*, 8 J. Vasc. Surg., 49 (1988); L. J. Dacey, et al., *Intraarterial 9-beta-methyl carbacyclin Improves Canine Polytetrafluoroethylene Graft Patency*, 8 J. Vasc. Surg., 21 (1988).

Potential infection and excessive inflammation can create problems with orthopedic prostheses. See e.g., E. J. Young and B. Sugarman, supra; S. P. F. Hughes, *Treatment of Infected Implants, Antibiotic Acrylic Composites*, 16 Orthopaedic Review, 233 (1987); J. H. Roth, et al., *Synovial Reaction Associated with Disruption of Polypropylene Braid-augmented Intraarticular Anterior Cruciate Ligament Reconstruction*, 16 Am.J. Sports Med., 301 (1988); S. K. Ahlfeld, et al., *Anterior Cruciate Reconstruction in the Chronically Unstable Knee using an Expanded Polytetrafluoroethylene (PTFE) Prosthetic Ligament*, 15 Am.J. Sports Med., 326 (1987).

Accordingly, the "take" of these implants, such as a cruciate ligament prosthesis, is variable.

Chemotherapeutic agents have been previously incorporated into vascular grafts. For example, U.S. Pat. No. 4,321,711 discloses a vascular prosthesis comprising porous tubing of polytetrafluoroethylene containing an anti-coagulant substance with a porous elastomer coating, containing a substance which counteracts the anti-coagulant, bonded to its outside surface. Typically, the anti-coagulant substance is heparin. Any heparin antagonist such as protamine may be used in the elastomer coating to counteract the heparin. U.S. Pat. No. 4,816,339 also refers to the use of therapeutically active substances, such as heparin or antibiotics, placed into an elastomer solution which surrounds a luminal polytetrafluoroethylene layer. However, the incorporated chemotherapeutic agents are soon exhausted from these implants, resulting in renewed potential for clotting. Thus, neither of these inventions provide for the sustained, controlled release of chemotherapeutic agents, nor the enhanced cellular uptake of these agents, that the present invention would provide.

The present invention solves these and many other problems associated with surgical implantation, successful grafting and tissue regeneration.

SUMMARY OF THE INVENTION

The present invention relates to a method of sustained, controlled delivery and enhanced uptake of microencapsulated chemotherapeutic and optional carrier agents incorporated into implants to localized treatment sites and tissues in a human or animal body. Also, implants incorporating microencapsulated chemotherapeutic agents and optional carrier agents are provided.

Accordingly, an advantage of one embodiment of the method of the present invention is to provide vascular grafts incorporating microencapsulated chemotherapeutic and optional carrier agents which upon implantation provide for sustained, controlled delivery and improved cellular uptake of anticoagulant agents at the implantation site such that the formation of blood clots (thrombi) are prevented. In addition, microencapsulated chemotherapeutic agents which act as an antagonist to the anticoagulant may be incorporated into an outer layer of the vascular graft.

An advantage of yet another embodiment is to provide prostheses incorporating microencapsulated chemotherapeutic agents and optional carrier agents, including for example, cruciate ligament prostheses, which upon implantation provide for sustained, controlled delivery and improved cellular uptake of antibiotic, anti-inflammatory and other appropriate agents to the implantation site, such that the retention of said prostheses is improved.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views, FIGS. 1A through 1D are diagrammatic perspective views of alternate configurations of microparticles which might be used in the present invention to contain chemotherapeutic agents or carrier agents;

FIGS. 2A through 2C are diagrammatic sectional views of alternate embodiments of microparticles having a somewhat spherical configuration with outside walls of varying thicknesses so as to provide for different timed release of chemotherapeutic or carrier agents from inside the microparticles;

FIG. 3 illustrates an example of a prior art vascular graph generally according to U.S. Pat. No. 4,321,711;

FIGS. 4A through 4D are end sectional views of vascular grafts illustrating alternate embodiments of vascular grafts showing various methods of incorporation of the microparticles into the vascular grafts;

FIG. 5 illustrates an embodiment of a cruciate ligament prosthesis incorporating microencapsulated chemotherapeutic and optional carrier agents in accordance with the principles of the present invention;

FIGS. 6A,B are an enlarged sectional view of a fiber bundle of the ligament prosthesis shown in FIG. 5, illustrating incorporation of the microencapsulated chemotherapeutic and optional carrier agents.

DETAILED DESCRIPTION OF THE INVENTION

Figure 7A:
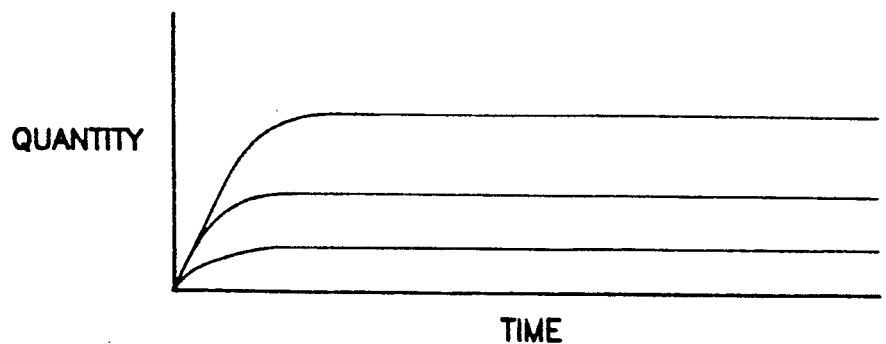
FIGS. 7A through 7D illustrate representative time release patterns of various chemotherapeutic agents which might be obtained by the appropriate microparticle configuration, microparticle arrangement in the implant, and chemotherapeutic agents used.

Referring now to FIGS. 1A-1D, time-release microparticles 10 containing chemotherapeutic and optional carrier agents 12, and incorporated into the matrix of the implants, including, but not limited to, grafts, prostheses, etc., of the present invention can occur in a variety of shapes and sizes.

The microparticles shown in FIGS. 1A-1D are greatly enlarged, and in actual use, might typically be less than a millimeter in size. As used herein, microparticles broadly include, without limitation, microspheres 14 (hollow and nonhollow), microfibers or microfibrils 16, hollow microfibers 18, microsponges 20, as well as any other microshape which incorporate chemotherapeutic and optional carrier agents into their body or matrix. An outer shell 22 of the microspheres 14 and the microfibers 16, an outer wall 24 of the hollow microspheres 14 and hollow microfibers 18, or matrix 26 of the microsponge 20 is composed of a biodegradable material, thereby allowing for the controlled, sustained release and improved cellular uptake of the chemotherapeutic agents over time.

In one embodiment, the microparticles are incorporated into the microstructure of the material comprising an implant according to the present invention. For example, the microspheres 14 can be contained within the mesh of fine fibrils connecting the matrix of nodes in expanded polytetrafluoroethylene (PTFE). In addition, somewhat larger microspheres can be meshed between layers of a multi-layered PTFE implant structure. The microspheres can be layered within the PTFE implant by adhesively positioning them onto the PTFE or by mixing them with a fluid and/or gel and flowing them into the netting or weave of the material. In such an embodiment, the fluid and gel can be carrier agents such as hyaluronic acid and a cross-linked gel of hyaluronic acid respectively. Finally, microspheres can also be positioned between the implant and an elastomer coating covering said implants.

In another embodiment, the microfibers or microfibrils can be woven into the mesh of the implant or, as described above, layered between successive layers of PTFE, or a similar material, comprising the implant.

In yet another embodiment, the microparticles may be in the form of microsponges which contain the desired chemotherapeutic and optional carrier agents within their microchanneling.

Microspheres between 10 and 700 microns in diameter are preferred. Various chemical and physical methods for preparing microspheres have been developed over the past twenty-five years and are well known to those skilled in the art. In this regard, see for example Patrick B. Deasy, *Microencapsulation and Related Drug Processes.* Marcel Dekker Inc., New York, 1984. Coacervation, interfacial polymerization, solvent evaporation and spray drying are examples of methods used in the production of microspheres which incorporate chemotherapeutic and optional carrier agents. Similarly, microfibers or microfibrils can be obtained for layering or weaving into the implant materials of the present invention. In this regard, hollow microfibers ranging in size from 100 to 1,000 microns in diameter can be produced and drug loaded by extrusion.

A wide variety of chemotherapeutic agents can be incorporated into the microshapes employed according to the method of the present invention. For example, antibacterial agents such as the bisbiguanides, antibiotics such as vancomycin or tetracycline, anti-inflammatory agents such as indomethacin or hydrocortisone, anticoagulants such as heparin and tissue regenerative agents such as fibronectin may be employed, depending upon the particular treatment or preventative goals sought.

Incorporation of the chemotherapeutic and optional carrier agents into the polymer comprising the microshape provides for a slow, sustained release and enhanced cellular uptake of the chemotherapeutic agent. The polymer matrix or carrier material chosen is preferably biodegradable, pharmaceutically acceptable and available in various grades to allow for variable control of the release rate of different chemotherapeutic agents. In this regard, it will be appreciated that the biodegradable materials utilized in time release capsules taken orally or other suitable biodegradable materials safe for use in the body or commonly known may be employed. For example, various biocompatible polymers can be employed, including but not limited to, collagen, cellulosic polymers, ethylene vinyl acetate, methacrylate polymers, lactic-glycolic acid copolymers, polycaprolactone, etc. In addition, polymers such as polystyrene, polycarbonate, polysulfone, polylactides and polyurethane can be employed. It will be appreciated that nonbiodegradable polymers incorporating chemotherapeutic agents are also within the scope of the present invention.

Carrier agents to improve cellular uptake of chemotherapeutic agents can also be incorporated into the implant. In one embodiment, the carrier agents can be mixed with the chemotherapeutic agents for delivery by the microparticles in the previously mentioned configurations. In another embodiment, the carrier agents can be separately incorporated into microparticles, which are then combined with the microparticles incorporating the chemotherapeutic agents. In yet another embodiment, the carrier agents can be in the form of a fluid or gel positioned within the weave or netting of the implant. In still another embodiment, a cross-linked, polymerized form of the carrier agent can be utilized to form the body of the implant.

Preferred carrier agents include, without limitation, hyaluronic acid, salts thereof such as sodium hyaluronate, esters, ethers, enzymatic derivatives and cross-linked gels of hyaluronic acid and chemically modified derivatives of hyaluronic acid such as hylan. As used herein, hyaluronic acid broadly refers to naturally occurring, microbial and synthetic derivatives of acidic polysaccharides of various molecular weights constituted by residues of D-glucuronic acid and N-acetyl-D-glucosamine.

Referring now to FIGS. 2A-2C, wherein is illustrated diagrammatic sectional views of alternative embodiments of microspheres in accordance with the present invention. The microspheres 10 have a polymer wall or shell 24 which surrounds the chemotherapeutic and optional carrier agents 12, or matrix containing the chemotherapeutic and optional carrier agents. Thus, the walls of the microspheres may have varying thicknesses and/or be made of a different material to provide for release of the agent continuously or periodically over an extended time period following surgical placement of the implant. For example, an implant may contain an antibiotic which would be released from one type of microparticle during the first critical days following graft placement, whereas an anti-inflammatory agent contained in a second type of microparticle would be released several weeks after implantation. In addition, it is to be understood that the chemotherapeutic and optional carrier agents contained within the microsphere may occur in any appropriate medium, such as aqueous, gelatinous, colloidal or semi-solid media. Furthermore, a carrier agent may also be provided with the microencapsulated chemotherapeutic agent to enhance the cellular uptake of the chemotherapeutic agent at the desired treatment site.

In another embodiment according to the method of the present invention, the chemotherapeutic and optional carrier agents are positioned at strategic areas of the implants relative to their intended function. For example, an anticoagulant substance could be positioned within the body or internal lining of a vascular graft, while a substance counteracting the anticoagulant would be positioned at the graft outer surface. In addition, a carrier agent can be included to enhance the cellular uptake of the anticoagulant and its antagonist. In a further modification, other chemotherapeutic agents can be positioned at different strategic areas of the implant materials relative to their intended uses. For example, an antibiotic, alone or in conjunction with a carrier agent, could be positioned near the attachment points of a ligament prosthesis, while an anti-inflammatory agent could be positioned within the body of the prosthesis.

Referring now to FIG. 3A, which illustrates a prior art drawing of a vascular graft according to U.S. Pat. No. 4,321,711 (Mano). The Mano vascular graft 28 incorporates chemotherapeutic agents, such as the anticoagulant heparin, directly into the body of the vascular graft 30, while incorporating a counteracting substance to the anticoagulant in the elastomer coating surrounding the body of the vascular graft 32.

In comparison, the vascular graft of the present invention may incorporate microencapsulated chemotherapeutic and optional carrier agents into the body of the vascular graft, between the layers comprising the graft or in an elastomer coating surrounding the body of the graft. Thus, in FIGS. 4A-4D there is illustrated cross-sectional views of vascular grafts 34 incorporating microencapsulated chemotherapeutic and optional carrier agents 10 in accordance with the method and implant of the present invention. In particular FIG. 4A depicts a cross-sectional view of a vascular graft 34 according to the method and implant of the present invention, wherein one microencapsulated chemotherapeutic agent 10, such as an anticoagulant, is incorporated into the inner layer of the graft 36. Conversely, another microencapsulated chemotherapeutic agent 10, such as an anticoagulant antagonist, is incorporated into the outer layer of the graft 40. Alternatively, as illustrated in FIG. 4B, a single incorporation of microencapsulated chemotherapeutic agents 10 may be placed between the layers comprising the graft 38. FIGS. 4C-4D illustrate further potential embodiments. For example, in FIG. 4C, microencapsulated chemotherapeutic agents 10 are only incorporated into the outer layer 40 of a vascular graft 34 in accordance with the present invention, whereas in FIG. 4D, a first microencapsulated chemotherapeutic agent 10 is incorporated into the inner layer 36 of a vascular graft 34 according to the present invention, while a second microencapsulated chemotherapeutic agent 10 is incorporated between the layers comprising the graft 38. It is to be understood that any additional potential combinations of microencapsulated chemotherapeutic agents, alone or in combination with optional carrier agents, which may be incorporated into any layers, or spaces between the layers, of a vascular or related graft are considered within the scope of this invention.

FIG. 5 illustrates a cruciate ligament prosthesis 44 incorporating microencapsulated chemotherapeutic and optional carrier agents according to the method and implant of the present invention. Such prostheses are made of bundled fibers 46, composed of materials such as PTFE, and are utilized in reconstructive surgery of injured knee joints. Preferred chemotherapeutic agents include antibiotics, such as vancomycin, which help to safeguard against threatening infections, such as staph infections, which would jeopardize the implant and surrounding tissue. Also preferred are anti-inflammatory agents, such as a nonsteroidal anti-inflammatory drug, which minimize post-surgical swelling and discomfort and expedite healing and renewal of normal function.

Illustrated in FIGS. 6A,B, are enlarged partial sectional views through a fiber bundle 46 of the cruciate ligament prosthesis 44 shown in FIG. 5, illustrating different configurations of microparticles being present. In particular, in FIG. 6A, the individual fibers 48 comprising the bundle 46 are interwoven with a matrix of chemotherapeutic and optional carrier agent encapsulating microfibers 16 or microfibrils 16 in accordance with the present invention. Alternatively, in FIG. 6B, the fibers 48 comprising the bundle 46 are surrounded by microspheres 14 incorporating chemotherapeutic and optional carrier agents.

Figure 7B:
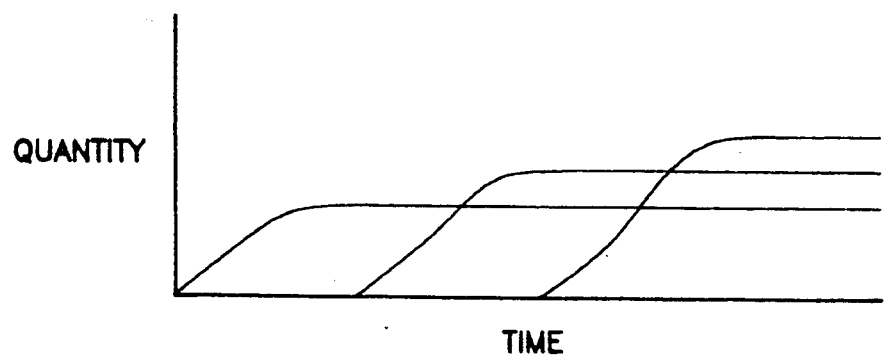
Figure 7C:
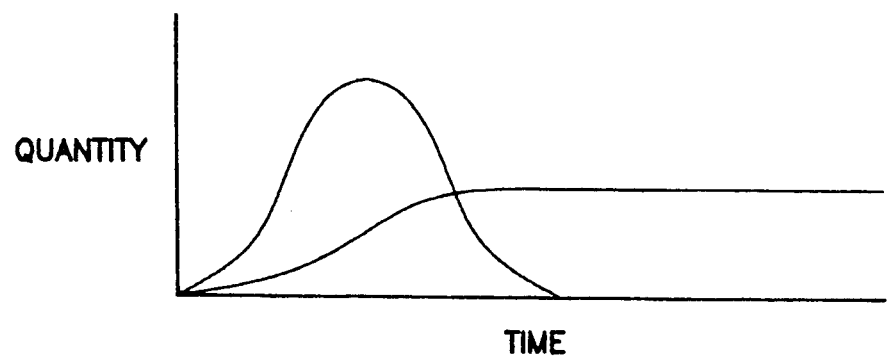
Figure 7D:
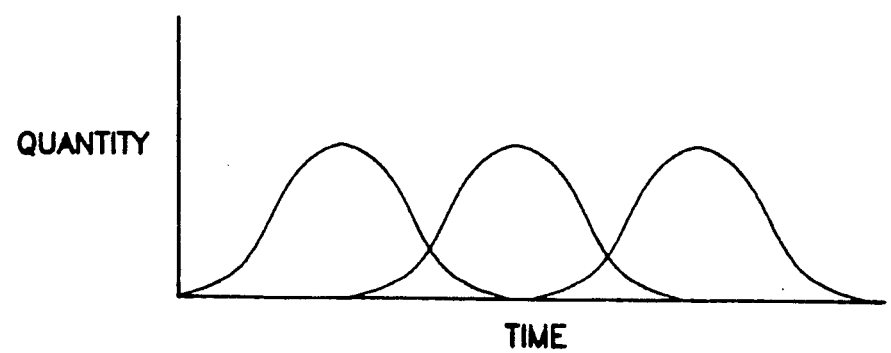

Illustrated in FIGS. 7A through 7D, are various chemotherapeutic agent release patterns which might be achieved using the principles of the present invention. The charts shown illustrate quantity or dosage of the chemotherapeutic agent released over time. In FIG. 7A, three separate chemotherapeutic agents are illustrated as being released at three different substantially constant levels. For example, an antibiotic, anti-inflammatory and tissue regenerative agent may all be released at varying levels at an implantation site. In FIG. 7B, three different chemotherapeutic agents are released at different times. Thus, in accordance with the previous example, the antibiotic may be released first to control post-operative infection, followed by the anti-inflammatory agent to control swelling, and finally a tissue regenerative agent to aid in healing. In FIG. 7C, a first chemotherapeutic agent is illustrated as being released very early in time and then a second chemotherapeutic agent is released at a substantially constant level for a sustained period of time. An initial high dose release of an antibiotic, followed by a sustained and lower release dose of an anti-inflammatory agent would be illustrative of such a release pattern. Finally, FIG. 7D illustrates three different chemotherapeutic agents being released at different times. Such an impulse release pattern may prove particularly useful with a drug which exhibits toxic effects at sustained high dosages or whose efficacy diminishes if administered continuously over a sustained period of time.

It will be appreciated that in addition to the method and implant described above, the method of the present invention may be utilized with a wide variety of other biomedical devices, including without limitation, vascular access devices, synthetic heart valve leaflets, tendon implants, transcutaneous access devices and artificial skin.

It will be further appreciated that the particular chemotherapeutic agents and optional carrier agents utilized, as well as the dosages and durations of treatment, will be in accordance with accepted treatment. The present invention addresses the manner in which the chemotherapeutic and optional carrier agents are delivered to the local treatment site.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

I claim:

1. A surgical implant comprising a porous matrix, said matrix further containing time-release microshapes encapsulating at least one chemotherapeutic agent incorporated into said porous matrix, wherein said time-release microshapes will begin to release said at least one chemotherapeutic agent at a localized treatment site upon surgical implantation of said implant, said implant further containing means for improving the cellular uptake of said at least one chemotherapeutic agent at the localized treatment site upon surgical implantation of said implant, said means comprising at least one carrier agent incorporated into the matrix of said implant, said implant selected from the group consisting of a vascular graft, heart valve leaflet, ligament prosthesis, tendon prosthesis and urethral prosthesis.

2. The surgical implant of claim 1 wherein the carrier agent is hyaluronic acid or a derivative thereof.

3. The surgical implant of claim 1 wherein the carrier agent is encapsulated in a time-release microshape.

4. The surgical implant of claim 1 wherein the carrier agent is mixed with the at least one chemotherapeutic agent and encapsulated in said time-release microshape prior to incorporating said time-release microshapes into said matrix of said implant.

5. The implant of claim 1 being constructed of a biodegradable, resorbable material.

6. The implant of claim 5, wherein said biodegradable, resorbable material is cross-linked collagen or an ester of hyaluronic acid.

* * * * *